United States Patent [19]

Ooe et al.

[11] Patent Number: 4,562,593
[45] Date of Patent: Dec. 31, 1985

[54] METHOD FOR DETERMINATION OF PERCENTAGE T CELL CONTENT OF LYMPHOCYTE

[75] Inventors: Akihiko Ooe, Komaki; Masaki Fuse, Nagoya, both of Japan

[73] Assignee: Mitsubishi Rayon Co., Ltd., Tokyo, Japan

[21] Appl. No.: 470,945

[22] Filed: Mar. 1, 1983

[30] Foreign Application Priority Data

Mar. 8, 1982 [JP] Japan .................. 57-36250

[51] Int. Cl.⁴ .............................................. G06K 9/00
[52] U.S. Cl. ........................................ 382/6; 364/416; 377/10
[58] Field of Search ................ 382/6, 27, 17; 356/39; 364/416; 377/6, 10

[56] References Cited

U.S. PATENT DOCUMENTS

| | | | |
|---|---|---|---|
| 3,214,574 | 10/1965 | Landsman et al. | 382/6 |
| 3,444,517 | 5/1969 | Rabinow | 382/17 |
| 3,705,383 | 12/1972 | Frayer | 382/6 |
| 4,082,457 | 4/1978 | Kohno et al. | 356/39 |
| 4,298,858 | 11/1981 | Romanski | 382/27 |
| 4,307,376 | 12/1981 | Miller et al. | 382/6 |
| 4,320,415 | 3/1982 | Jones | 382/6 |
| 4,330,884 | 5/1982 | Obata et al. | 369/255 |
| 4,425,237 | 1/1984 | Abe et al. | 210/927 |

FOREIGN PATENT DOCUMENTS

| | | | |
|---|---|---|---|
| 51-1192 | 1/1976 | Japan | 382/6 |
| 51-98092 | 8/1976 | Japan | 382/6 |
| 55-12431 | 1/1980 | Japan | 382/6 |

OTHER PUBLICATIONS

Lehninger, *Biochemistry, the Molecular Basis of Cell Structure and Function*, second edition, Chapter 35, pp. 1004–1006.

*Primary Examiner*—Leo H. Boudreau
*Assistant Examiner*—Joseph Mancuso
*Attorney, Agent, or Firm*—Oblon, Fisher, Spivak, McClelland & Maier

[57] ABSTRACT

A method for determining the percentage T-cell content of lymphocyte, which comprises scanning a test specimen with a pickup device, discriminating a lymphocyte from other cells contained in said specimen from the output level and regional information of the image signals transmitted from said pickup device, searching the data marginal to those of the cell discriminated as lymphocyte, to detect pixels corresponding to the image signal output level different from that corresponding to the lymphocytes or background, and discriminating a T-cell from other lymphocytes from the number of detected pixels.

10 Claims, 4 Drawing Figures a) MICROSCOPIC IMAGE i) CLUSTERED T CELLS.

ii) LYMPHOCYTE OTHER THAN T CELL.

b) CELL DATA BY DOUBLE-THRESHOLD PROCESSING.

i) CLUSTERED T CELLS.

ii) LYMPHOCYTE OTHER THAN T CELL.

METHOD FOR DETERMINATION OF PERCENTAGE T CELL CONTENT OF LYMPHOCYTE

This invention relates to a method for the determination of the percentage T cell content of lymphocyte utilizng an image processing technique.

The variation in number and the metaplasia of lymphocyte, a member of leucocyte family, have long been utilized successfully in the diagnosis of infections diseases such as whooping cough and, more recently, with the advance in the analysis of lymphocytes, the elucidation of newly-found diseases such as immunodeficiency is now being in progress.

Lymphocytes are classified from the standpoint of their function into T cells, B cells and Null cells. The ratios among these cells remain substantially constant in normal subjects, whereas they are liable to variation in patients. Since the test for the percentage T cell content of lymphocyte has been quite recently introduced into the diagnostic practice, an automatic equipment for test has not yet been reported. A typical test procedure now in use is based on the microscopic observation by an examination specialist performed on a specimen prepared by the E rosette method. The test procedure comprises the following steps:

(a) Extraction of lymphocytes: a collected blood sample containing heparin is admixed with a phosphate buffer saline and Conray-Ficol and centrifuged to extract lymphocytes;

(b) Adjustment of the number of lymphocytes: the number of lymphocytes is counted by means of a counting chamber and the concentration in the specimen is adjusted to facilitate the operation in the succeeding steps;

(c) Formation of rosette: after addition of sheep erythrocytes, the lymphocyte-containing liquor is cultivated to form a rossette of T cells;

(d) Coating on slide glass: a smear sample was spread over a slide glass, then dried, and stained with safranine; and (e) Microscopic examination: 200 lymphocytes of the smear are counted by an examination specialist under a microscope and the percentage of T cells attached with sheep erythrocytes is determined.

This invention is directed to the automation of the last step (e) involving the microscopic examination in the procedure described above.

The present inventors already proposed an equipment for the determination of percentage T cell content of lymphocyte (Japanese Patent Application No. 174,015/81). This equipment utilizes as the scanner a high-resolution pickup element of the line scanning type which reads all picture elements (pixels) along one axis at each stroke and the output signals are processed continuously stroke by stroke to determine the number of cells. By such means it has become possible to overcome the difficulties encountered in practicing the conventional technique which is time-consuming, complicated in operation, deficient in precision, and susceptible to the phenomenon of residual image. This equipment for the determination of percentage T cell content of lymphocyte comprises an automatic feeding mechanism which allows the specimen to move at a constant speed, while being regulated for the focal point; a solid-state pickup element of the line scanner type which is disposed so as to read the specimen in a direction perpendicular to the direction of movement of the specimen; a measuring circuit to detect the shape of cells from the image signals transmitted from said pickup element, and discriminate the T cells from other lymphocytes as well as the lymphocytes from other cells; counters for the T cells and for other lymphocytes; and a circuit to display the percentage T cell content.

The above equipment is illustrated in further detail with reference to the accompanying drawings. FIG. 1 is a block diagram to illustrate the equipment and the procedure of determination. The specimen (1) is a smear of the sample which is prepared by the E rosette method and spread on a slide glass in a stripe of 1 to 2 mm in width, then fixed, and stained. In preparing the specimen (1), the blood or erythrocytes of sheep is mixed with the sample of human blood or suspended hemocytes to allow the sheep erythrocytes to adhere preferentially to the T cells, thus facilitating the discrimination of T cells from other hemocyte constituents. The specimen (1) is allowed to move by means of an automatic feeding mechanism (7), while being adjusted for focal point by an automatic focusing mechanism (9). Among automatic focusing means, micrometer method using air system (a method wherein, by blowing air to keep the back pressure of the blowing air constant, the distance between specimen and nozzle is kept constant) is preferred to others such as image signal analysis, light quantity checking, and touch sensing. The pickup element of the line scanner type (3) reads the specimen (1) through an optical system (2) and transmits the image signal in accordance with the luminance. The measuring circuit (4) converts the analog information received from the pickup element (3) into a digital information. Further, it measures the shape of each cell contained in the specimen (1) and discriminates T cells, other lymphocytes, and other cells from one another. The shape factors employed as the criteria of discrimination include horizontal length, vertical length, area, peripheral length, average concentration, and N-to-C ratio (the ratio of nucleus area to plasma area) of each cell. The cells other than lymphocytes include sheep erythrocytes, human erythrocytes, and leucocytes other than lymphocytes. The counter circuit (5) counts T cells and lymphocytes other than T cells. After 200 counts, one half of the number of T cells is transmitted to the percentage T cell content display circuit (6). The control unit (8) serves to synchronize the processing speed in each part of the equipment.

This invention relates to an improvement in the method of determining the percentage T cell content of lymphocytes which is carried out as described above.

When observed under a microscope, the specimen shows a colored pattern comprising A. colorless background, B. erythrocytes of sheep and man in pale yellowish brown color, and C. lymphocytes and granulocytes in red color.

In order to discriminate precisely the cells, it is necessary to classify the image signals transmitted from a pickup device such as the line scanner-type solid-state pickup element into 3 groups according to the output levels corresponding to A, B and C, then determine the representative value of each group (hereinafter such a procedure is referred to as "double threshold processing"), and measure the regions B and C. However, to carry out successfully such a procedure, it is necessary to overcome the following three difficulties:

1. The number of cells contained in the specimen includes about 15,000 sheep erythrocytes and several hundreds of other cells for every 200 lymphocytes. Therefore, if the cells belonging to the regions B and C are to be measured without discrimination, it becomes necessary to measure a great number of sheep erythrocytes scattered all over the specimen, though the required data are only those of cells B attached to C cells.

2. Among various cells contained in the specimen, T cells are most liable to agglomeration. In the case where a number of C cells gather together with interposed B cells to form clusters, it is difficult to count T cells contained in the cluster if the regions B and C are simultaneously measured. To avoid the detection error resulting from such a measurement, it becomes necessary to employ a complicated procedure.

3. In double threshold processing of image signals, the value of output level is in the order of $A<B<C$. Even if there is no sheep erythrocyte around a lymphocyte corresponding to C, the pixel in the boundary region of C is frequently composed partly of region C and partly of region A and, in some cases depending upon the ratio of area between C and A, the value of output level of such a pixel becomes equivalent to that of region B, leading to false information that the region B has been detected.

This invention is predicated upon the discovery that the above difficulties can be overcome by subjecting the image signals transmitted from the pickup element to double threshold processing in accordance with the output levels corresponding to A, B and C, detecting the region corresponding to C, selecting the lymphocytes on the basis of regional information obtained from region C, and measuring the region B in the vicinity of the region corresponding to the lymphocyte.

This invention provides a method of determining the percentage T cell content of lymphocyte, which comprises analyzing the output level and regional information of the image signal transmitted from a pickup element to discriminate the lymphocyte (region C) among the cells contained in a specimen, determining the number of pixels pertaining to the region B from the data on the region in the vicinity of said lymphocyte to discriminate T cells. The term "regional information", as herein used, means the information necessary to discriminate the lymphocyte and granulocyte, such as area of the region and total concentration, that is, total value of the outputs of the region.

The invention is illustrated below in detail with reference to the accompanying drawings.

Figure 4:
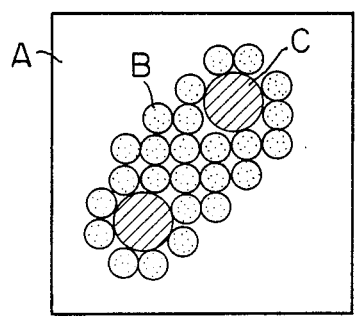
FIG. 4 are schematic drawings to illustrate the advantages of this invention.
Figure 4:
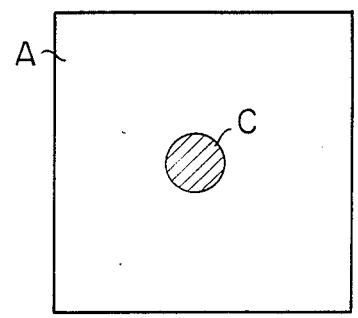
Figure 4:
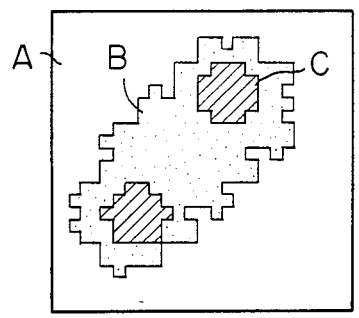
Figure 4:
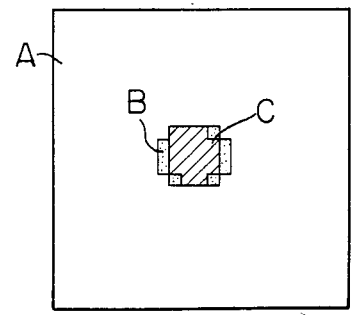

In FIG. 4, (a) is the microscopic image and (b) is cell data obtained by double threshold processing.

In the above figures, 1: specimen; 2: optical system; 3: solid-state pickup element of the line scanner type; 4: measuring circuit; 5: counter circuit; 6: display circuit for the percentage T cell content; 7: automatic feeding mechanism; 8: control unit; 9: automatic focusing mechanism; A: background; B: sheep or human erythrocyte; C: lymphocyte; (i): clustered T cell; (ii): lymphocyte other than T cell.

The specimen 1 is prepared by coating on a slide glass a sample made by the method of E rosette in a stripe of 1 to 2 mm in width, then fixing, and staining. The specimen 1 is allowed to pass across the field of view of an optical system 2 by means of an automatic feeding mechanism 7 across the field of view of the optical system 2, while the focal point being adjusted by an automatic focussing mechanism 9. A solid-state pickup element of the scanner type 3 reads the specimen 1 through the optical system 2 and transmits the image information in accordance with the luminance. The measuring circuit 4 converts the analog information from the pickup element 3 into a digital one and, based on this regional information, discriminates lymphocyte from other cells and T cell from other lymphocytes among the cells contained in the specimen 1. The counter circuit 5 counts T cells and other lymphocytes. When 200 of T cells and other lymphocytes have been counted, one half of the number of T cells is transmitted to a display circuit 6 for the percentage T cell content. A control unit 8 serves to synchronize the processing speed in each unit.

The method of cell discrimination according to this invention is illustrated below.

At first the measurement is performed on the region C, neglecting the region B, to provide regional information and, based on this information, judgement is performed whether or not the pixel belongs to the region of lymphocyte. When the pixel is judged to belong to the lymphocyte region, examination is performed whether or not a sheep erythrocyte is attached to the lymphocyte. For this purpose, each pixel apart by 1 pixel outward from the lymphocyte (for example, $Y_e+2$ and $Y_s-2$ in FIG. 2) is examined whether or not it belongs to the region B, because a pixel adjacent to a lymphocyte sometimes contains both regions of lymphocyte (C) and background (A), and may be mistaken for another belonging to the region B. In this way, the third of the aforementioned difficulties is eliminated.

The size of pixel scanned by the pickup element may be varied according to the purpose of measurement by varying the combination of magnification in the optical system 2 and width of the scanning line. It is desirable that at least two pixels be required in one direction for the measurement of one sheep erythrocyte. Since the size of a sheep erythrocyte is 3 to 4 μm, the size of a pixel is preferably about 1 μm. However, it is obvious that the pixel size is not limited to such a range in consideration of the case where a large number of sheep erythrocytes are attached to a T-type lymphocyte. The method of examining pixels apart by 1 pixel outward from the lymphocyte region is illustrated below with reference to FIGS. 2 and 3.

Figure 1:
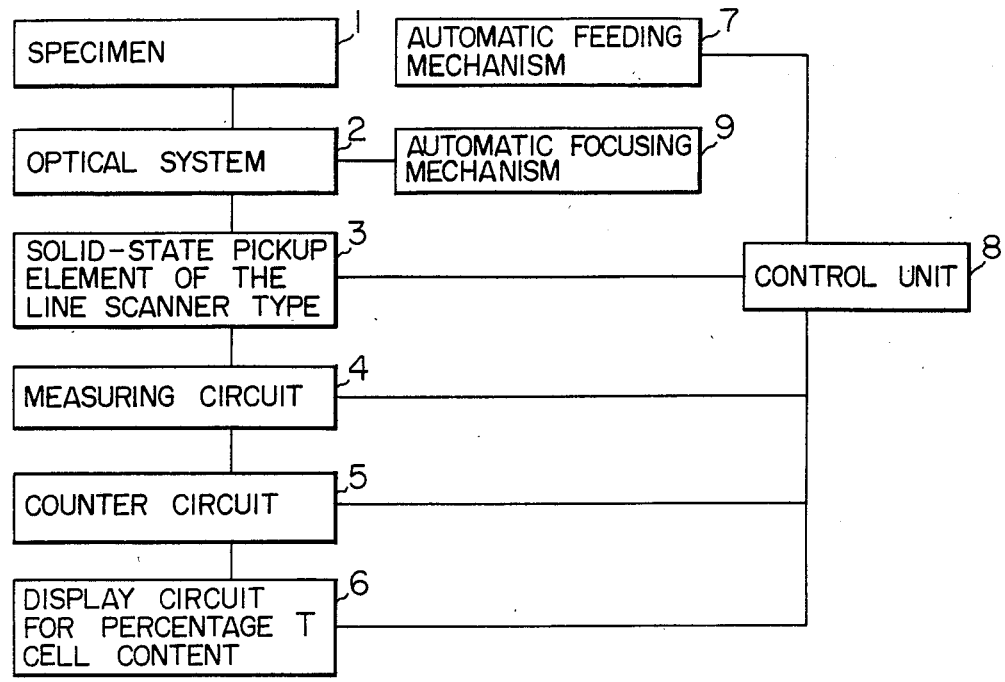
FIG. 1 is a block diagram to illustrate the equipment and the method of determination according to this invention.
Figure 2:
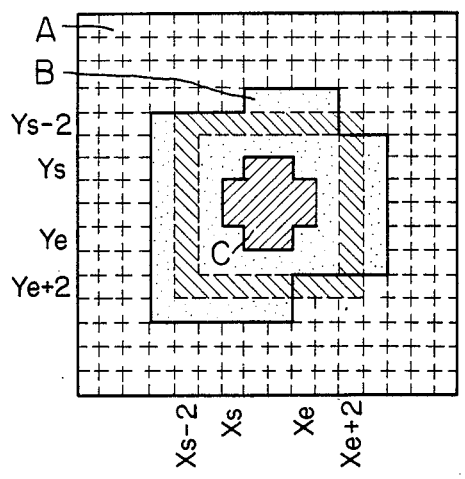
FIGS. 2 and 3 are schematic drawings to illustrate the method of cell discrimination according to this invention.
Figure 3:
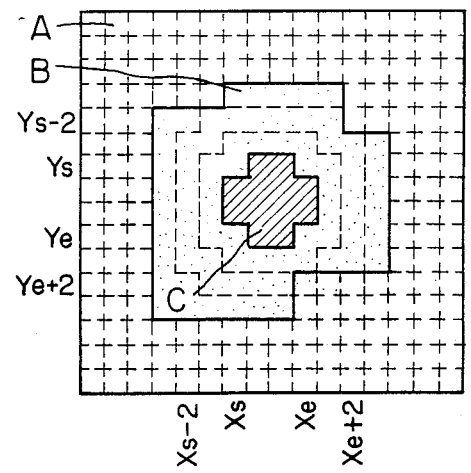

In FIGS. 2 and 3, each minute square element of the checker pattern is a pixel. A, B and C are pixels belonging to the regions of background, sheep erythrocyte, and lymphocyte, respectively. $y_s$ and $y_e$ are the pixels detected at first and at last, respectively, in the direction of ordinate as a pixel included in the lymphocyte at the scanning (the pixels appearing at the highest and the lowest of the lymphocyte in FIGS. 2 and 3), and $x_s$ and $x_e$ are the pixels detected at first and at last, respectively, in the direction of abscissa as a pixel included in the lymphocyte at the scanning (the pixels appearing at the leftmost and rightmost of the lymphocyte in FIGS. 2 and 3). In FIG. 2, the area enclosed by the 2 sets of thick broken lines indicates those pixels which correspond to the sides and vertices of a square represented by the pixels corresponding to vertices $(x_{s-2}, y_{s-2})$, $(x_{s-2}, y_{e+2})$, $(x_{e+2}, Y_{s-2})$ and $(x_{e+2}, y_{e+2})$, within the assembly of pixels belonging to the region C. In FIG. 3, there are shown pixels of the region enclosing boundary regions including regions of vertices of the square shown in FIG. 2, for the purpose of scrutinizing more precisely the pixels apart by 1 pixel outward from the boundary of the lymphocyte region.

The pixels belonging to the region enclosed by the thick broken lines are examined and the number of pixels exhibiting an output level corresponding to that of region B, which is the region of erythrocyte, is counted in order to discriminate the T cell from other lymphocyte cells. The methods shown in FIG. 2 and FIG. 3 are characterized by being such that the latter has a tendency to increase the precision, while the former is favorable to more rapid processing.

The advantages of this invention are described below with reference to FIG. 4.

In FIG. 4(a), (i) and (ii) represent microscopic images of an agglomerate of two T-cells and a lymphocyte other than T cell, respectively. FIG. 4(b) shows models constructed from the data of cells provided by the double-threshold processing of the image signals from the pickup element. In model (i), there are shown one region B and two regions C. Since at first only the region C is counted the count of lymphocytes is two. Because of the presence of the region B corresponding to sheep erythrocytes around the lymphocytes in question, these lymphocytes are judged to be T cells. The model (ii) shows the case where some zones over the regions A and C having a width corresponding to one pixel exists around the region C and these zones are liable to be mistaken for the region B. However, according to this invention, at first only the region C is detected, this model is counted as lymphocyte. Since the region B is measured in the outer zone apart from the boundary by one pixel, the zone belong to the boundary is not searched.

As described above, the method of this invention is suitable and advantageous for the determination of percentage T cell content of lymphocyte.

What is claimed is:

1. A fully automatic method for determining the percentage T-cell content of lymphocytes which have been sampled wherein said lymphocytes comprise T-cells, B-cells and Null-cells, said method comprising scanning a test specimen with a pick up device to produce image signals, discriminating a lymphocyte from other cells contained in said specimen from the output level and regional information of the image signals, searching the data marginal to those of the cells discriminated as a lymphocyte to detect pixels corresponding to the image signal output level different from that corresponding to the lymphocytes or background, discriminating a T-cell from other lymphocytes from the number of detected pixels, and determining and displaying the percentage T-cell content of said lymphocytes.

2. A method for determining the percentage T-cell content of lymphocyte according to claim 1, wherein the marginal data are the data of pixels apart by one pixel outward from the pixels corresponding to the cell discriminated as a lymphocyte.

3. A method for determining the percentage T-cell content of lymphocyte according to claim 1, wherein the marginal data are the data of pixels apart by one pixel outward from the rectangle circumscribing the pixels corresponding to the cell discriminated as a lymphocyte.

4. The method of claim 1 wherein the sampling of lymphocytes is performed manually.

5. The method of claim 1, wherein the image signals transmitted from the pickup device are subjected to double threshold processing.

6. The method of claim 1, wherein the image signals transmitted from the pick up device are subjected to double threshold processing in accordance with output levels corresponding to colorless background (A), pale yellowish-brown colored sheep or man erythrocytes (B), and red colored lymphocytes and granulocytes (C), where the value of the output level is in the order of $A<B<C$.

7. The method of claim 6 wherein at least one region corresponding to C is detected, lymphocytes are selected on the basis of regional information obtained from region C, and a region B is measured in the vicinity of the region corresponding to a lymphocyte to discriminate T-cells in a lymphocyte sample.

8. The method of claim 6, wherein at least one region corresponding to C is detected, neglecting regions B, resulting in the selection of a lymphocyte, then examining each pixel apart by one pixel outward from the lymphocyte to determine if such pixel belongs to a region B.

9. The method of claim 1, wherein at least two pixels are required, in one direction, for the measurement of one sheep erythrocyte.

10. The method of claim 1, wherein the pixel size is on the order of 1 μm.

* * * * *